Figure 1:
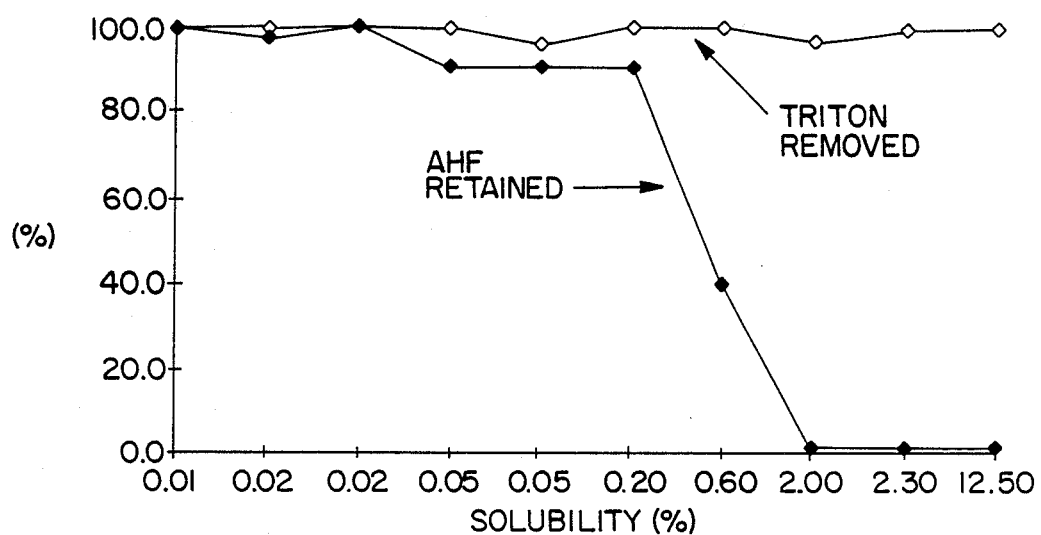

United States Patent [19]

Horowitz et al.

[11] Patent Number: 4,909,940
[45] Date of Patent: Mar. 20, 1990

[54] EXTRACTION OF PROCESS CHEMICALS FROM LABILE BIOLOGICAL MIXTURES WITH ORGANIC ALCOHOLS OR WITH HALOGENATED HYDROCARBONS

[75] Inventors: Bernard Horowitz, New Rochelle; Richard J. Bonomo, Hartsdale, both of N.Y.

[73] Assignee: New York Blood Center, Inc., New York, N.Y.

[21] Appl. No.: 139,502

[22] Filed: Dec. 30, 1987

[51] Int. Cl.$^4$ ............................................. B01D 11/04
[52] U.S. Cl. .................................... 210/634; 210/782; 210/804; 424/101; 494/37
[58] Field of Search ............... 210/638, 639, 702, 710, 210/781, 782, 800, 804, 634; 494/37; 604/4; 424/101

[56] References Cited

U.S. PATENT DOCUMENTS

| | | | |
|---|---|---|---|
| 3,958,939 | 5/1976 | Jones | 210/634 |
| 4,481,189 | 11/1984 | Prince | 424/101 |
| 4,540,573 | 9/1985 | Neuvath et al. | 424/101 |
| 4,721,730 | 1/1988 | Furuyoshi et al. | 210/679 |

OTHER PUBLICATIONS

E. Tabor, D. L. Aronson, R. J. Gerety, "Removal of Hepatitis B Virus Infectivity from Factor OX Complex by Hepatitis B Immune Globulin", *Lancet*, (1980), 2, 68–70.
H. G. J. Brummelhuis, J. Over, L. A. Duivis-Vorst et al, "Contributions to the Optimal Use of Human Blood, IX Elimination of Hepatitis B Transmission by (Potentially) Infectious Plasma Derivatives", *Vox San*, (1983) 45, 205–216.
J. W. Oliphant, A. Hollaender, "Homologous Serum Janudice Experimental Inactivation of Etiologic Agent in Serum by Ultraviolet Irradiation", *Public Health Rep.*, (1945), 61, 598–602.
S. S. Gellis, J. R. Neefe, J. Stokes Jr. et al., "Chemical, Clinical and Immunological Studies on the Products of Human Plasma Fractionation, XXXVI Inactivation of the Virus of Homologous Serum Hepatitis in Solutions of Normal Human Serum Albumin by Menas of Heat", *J. Clin. Invest.*, (1984), 27, 239–244.
R. Murray, W. C. L. Diefenbach, "Effect of Heat on the Agent of Homologous Serum Hepatitis", *Proc. Soc. Exp. Biol. Med.*, (1953), 84, 230–231.
J. P. Soulier, C. Blatix, A. M. Courouce et al, "Prevention of Virus B Hepatitis (SH) Hepatitis)", *Am. J. Dis. Chid.*, (1972), 123, 429–434.
T. Shikata, T. Karasawa, K. Abe et al, "Incomplete Inactivation of Hepatitis B Virus After Heat-Treatment at 60° C. for 10 hours", *J. Infect. Dis.*, (1978), 138, 242–244.
E. Tabor, R. J. Gerety, "The Chimpanzee Animal Model for non-A non-B Hepatitis: New Applications", W. Szmuness, H. J. Alter, J. E. Maynard eds. *Viral Hepatitis: 1981 International Symposium.*, Philadelphia: The Franklin Institute Press, (1981), 305–317.
Von N. Heimburger, H. Schwinn, P. Gratz et al, "Faktor VIII-Konzentrate, Hochgereinigt und in Losung Erhitzt, *Arzneim-Thromb/Drug Res.*, (1981), 31, 619.
F. O. MacCallum, "Homologous Serum Hepatitis", *Proc. Roy. Soc. Med.*, (1946), 39, 655.

(List continued on next page.)

Primary Examiner—W. Gary Jones
Attorney, Agent, or Firm—Sprung Horn Kramer & Woods

[57] ABSTRACT

A method of removing lipid soluble chemicals from a biological material containing the lipid soluble chemicals comprising bringing the biological material containing the lipid soluble chemicals into contact with an effective amount of an organic alcohol whose solubility in an aqueous solution at the temperature of use is $\leq 0.6\%$ and/or a halogenated hydrocarbon having more than one type of halogen, agitating the resultant mixture and achieving a phase separation of the biological material and the organic alcohol and/or halogenated hydrocarbon. The method is particularly useful for producing relatively virus free physiologically acceptable plasma.

11 Claims, 1 Drawing Sheet

OTHER PUBLICATIONS

R. Murray, J. W. Oliphant, J. T. Tripp et al, "Effect of Ultraviolet Radiation on Infectivity of Icterogenic Plasma, *JAMA*, (1955), 157, 8–14.

F. W. Hartman, G. A. LoGrippo, "Combined beta-Propiolactone and Ultraviolet Irradiation for Plasma Sterilization", F. W. Hartman, G. A. LoGrippo, J. G. Mateer et al, eds. *Hepatitis Frontiers, Henry Ford Hosp. International Symposium*, Boston, Little, Brown & Co., (1957), 407–416.

R. Kotitschke, W. Stephan, "Kominierte Behandlung von Gerinnungsfaktoren in Humanplasma mit β-Bropiolacton and UV, Struktur und Funktion des Fibrinogens", H. Schroeer, G. Hauck, F. Zimmerman et al, eds., *Blutgerinnung und Mikrozirkulation Stuttgart: Verlag*, (1986), 222–228.

G. A. LoGrippo, H. Hayashi, "Efficacy of beta-Propiolactone with Ultraviolet Irradiation of Hepatitis B Antigen in Human Plasma Pools, *Henry Ford Hosp. Med. J.*, (1973), 21, 181–186.

D. Heinrich, H. Berthold, "Application of Cold Sterilized Prothrombin Complex Concentrates in Man: Clinical and Serological Studies", The 13th International Congress of the World Federation of Hemophilia, Tel Aviv, Jul. 8–13, 1979.

A. M. Prince, B. Horowitz and B. Brotman, "Sterilization of Hepatitis and HTLV-III Viruses By Exposure to Tri(n-Butyl)Phosphate and Sodium Cholate", The Lancet, 706–710, Mar. 29, 1986.

S. M. Feinstone, K. B. Mihalik, T. Kamimura et al, "Inactivation of Hepatitis B Virus and non-A, non-B Hepatitis By Chloroform", *Infect. Immunol.*, (1983), 41, 816–821.

D. W. Bradley, J. E. Maynard, H. Popper et al, "Posttransfusion non-A, non-B Hepatitis: Physiochemical Properties of Two Distinct Agents", *J. Infect. Dis.*, (1983), 148, 254–265.

F. B. Hollinger, G. Dolana, W. Thomas et al, "Reduction in Rish of Hepatitis Transmission by Heat-Treatment of a Human Factor VIII Concentrate", *J. Infect. Dis.*, (1984) 150, 250–262.

A. M. Prince, B. Horowitz, B. Brotman et al, "Inactivation of Hepatitis B and Hutchinson Strain non-A, non-B Hepatitis Viruses by Exposure to Tween 80 and Ether", *Vox Sang*, (1984), 46, 36–43.

E. Tabor, G. Murano, P. Snoy et al, "Inactivation of Hepatitis B Virus by Heat in Antithrombin III Stabilized with Citrate", *Thromb. Res.*, (1981), 22, 233–238.

D. Menache, D. L. Aronson, "Measures to Inactivate Viral Contaminants of Pooled Plasma Products, R. Y. Dodd, L. F. Baker eds, *Infection Immunity and Blood Transfusion Proc. XVII Annual Scientific Symposium*, May 9–11, 1984, N.Y., Alan R. Loss, (1985), 407–423.

C. Rouzioux, S. Chamaret, L. Montagnier, V. Carnelli, G. Rolland, P. M. Mannucci, "Absence of Antibodies to AIDS Virus in Haemophiliacs Treated with Heat-Treated Factor VIII Concentrate, *Lancet*, (1985), February, 271–272.

M. Colombo, V. Carnelli, C. Gazengel, P. M. Mannucci, G. F. Savidge, K. Schimpf, "Transmission of non-A, non-B Hepatitis by Heat-Treated Factor VIII Concentrate", *Lancet*, (1985), Jul. 1–4.

W. Stephan, A. M. Prince, "Efficacy of Combined Treatment of Factor IX Complex (PPSB) with B-Propiolactone (b-PL) and Ultraviolet (UV) Irradiation", *Haemostasis*, (1981), 10, 67.

A. M. Prince, W. Stephan, B. Brotman, "B-Propiolactone/Ultraviolet Irradiation: A Review of its Effectiveness for Inactivation of Viruses in Blood Derivatives", *Rev. Infect. Dis.*, (1983), 5, 92–107.

W. Stephan, A. M. Prince and R. Kotitschke, "Factor VIII Concentrate from Cold Sterilized Human Plasma", *Develop Biol. Stand*, (1983), 54, 491.

The LANCET, Sep. 28, 1985, p. 721, "Wet Heating for Safer Factor VIII Concentrate".

Viral Hepatitis: Second International Max von Pettenkofer Symposium, Marcel Dekker, Inc. New York and Basel, "Reduction of Infectivity of Hepatitis B Virus (HBV) and a Non-A, Non-B Hepatitis Agent By Heat Treatment of Human Anthihemophilic Factor (AHF) Concentrates", pp. 245–246, F. B. Hollinger, et al.

The Lancet, Jul. 27, 1985, p. 213, "Non-A, Non-B Hepatitis and Heat-Treated Factor VIII Concentrates".

A. Helenius and K. Sinous, "Solubilization of Membranes by Detergents", Biochem. Biophys. ACTA, (1975), 415, 29–79.

N. Heimburger, H. Schwinn, R. Mauler, "Factor VIII Concentrate, Hepatitis-Safe: Progress in the Treatment (List continued on next page.)

OTHER PUBLICATIONS of Hemophilia A", *Die Gelben Hefte,* (1980), 20, 165–174 (including English language translation thereof).

Y. K. Yip, R. H. L. Pang, J. O. Oppenheim, M. S. Nashbar, D. Henriksen, T. Zerebecky]-Eckhardt, J. Vilcek, "Stimulation of Human Gamma Interferon Production by Diterpene Esters", *Infect. and Immun.,* (1981), 131–139.

B. D. Williamson, E. A. Carswell, B. Y. Rubin, J. S. Prendergast, H. J. Old, "Human Tumor Necrosis Factor Produced by Human B-cells Lines: Synergistic Cytoxic Interaction with Human Interferon", *Proc. Natl. Acad. Sci., U.S.A.,* (1983), 80.

B. Y. Rubin, S. L. Anderson, S. A. Sullivan, B. D. Williamson, E. A. Carswell, L. J. Old, "Purification and Characterization of a Human Tumor Necrosis Factor from the LukII Cell Line", *Proc. Natl. Acad. Sci., U.S.A.,* (1985), 82, 6637–6641.

G. Dolana, D. Tse, W. Thomas et al, "Hepatitis Risk Reduction in Hemophilia: A Heated Factor VIII Preparation", *Blood,* Abstract 768 (1982), Supp. 1, 210a.

EXTRACTION OF PROCESS CHEMICALS FROM LABILE BIOLOGICAL MIXTURES WITH ORGANIC ALCOHOLS OR WITH HALOGENATED HYDROCARBONS

BACKGROUND OF THE INVENTION

1. Field of the Invention

The present invention concerns the processing of biological mixtures through extraction of those mixtures with organic alcohols and/or halogenated hydrocarbons in order to remove exogenous or endogenous lipid soluble chemicals, for example, chemicals used in the inactivation of viruses. The present invention also concerns protein-containing blood products having an extent of inactivation of virus greater than 6 logs for the virus and having a retention of functional activity for particular biological blood proteins of at least 45%.

2. Background Information

Blood can contain each of several different viruses including but not limited to hepatitis B virus (HBV), non-A, non-B hepatitis virus (NANBHV), cytomegalovirus, and immunodeficiency viruses. It is highly desirable to inactivate these viruses in the course of preparing vaccines and prior to the therapeutic application of blood and blood fractions. Both physical (e.g., heat, irradiation) and chemical (e.g., aldehydes, organic solvents, detergents, etc.) methods have been used to inactivate viruses such as HBV in mammalian blood and blood fractions. Inactivation renders a virus non-infectious and non-pathogenic.

Numerous attempts have been made to inactivate viruses such as hepatitis B virus (HBV) in mammalian, especially human, blood plasma. It is the practice in some countries to effect inactivation of the hepatitis B virus in the blood plasma by bringing the plasma into contact with a viral inactivating agent which crosslinks the proteinaceous portions of hepatitis B virus or which interacts with the nucleic acid of the virus. For instance, it is known that hepatitis B virus is inactivated by contact with an aldehyde, such as formaldehyde.

Procedures that have been tested for inactivating viruses in protein biologics include the following:

(1) neutralization with specific antibodies (E. Tabor, D. L. Aronson, R. J. Gerety, "Removal of Hepatitis B Virus Infectivity from Factor IX Complex by Hepatitis B Immune Globulin", Lancet, (1980), 2, 68-70; H. G. J. Brummelhuis, J. Over, L. A. Duivis-Vorst et al, "Contributions to the Optimal Use of Human Blood. IX->Elimination of Hepatitis B Transmission by (Potentially) Infectious Plasma Derivatives", Vox San, (1983), 45, 205-216), (2) ultraviolet irradiation ("UV") (J. W. Oliphant, A. Hollaender, "Homologous Serum Jaundice Experimental Inactivation of Etiologic Agent in Serum by Ultraviolet Irradiation", Public Health Rep., (1945), 61, 598-602; F. O. MacCallum, "Homologous Serum Hepatitis", Proc. Roy. Soc. Med., (1946), 39, 655; R. Murray, J. W. Oliphant, J. T. Tripp et al, "Effect of Ultraviolet Radiation on the Infectivity of Icterogenic Plasma, JAMA, (1955), 157, 8-14), (3) beta-propiolactone ("BPL") and ultraviolet (UV) radiation (F. W. Hartman, G. A. LoGrippo, "Combined beta-Propiolactone and Ultraviolet Irradiation for Plasma Sterilization", F. W. Hartman, G. A. LoGrippo, J. G. Mateer et al, eds. Hepatitis Frontiers. Henry Ford Hosp. International Symposium, Boston, Little, Brown & Co., (1957), 407-416; R. Kotitschke, W. Stephan, "Kominierte Behandlung von Gerinnungsfaktoren in Humanplasma mit β-Propiolacton and UV. Struktur und Funktion des Fibrinogens", H. Schroeer, G. Hauck, F. Zimmerman et al, eds., Blutgerinnung und Mikrozirkulation Stuttgart: Verlag, (1976), 222-228; G. A. LoGrippo, H. Hayashi, "Efficacy of beta-Propiolactone with Ultraviolet Irradiation of Hepatitis B Antigen in Human Plasma Pools, Henry Ford Hosp. Med. J., (1973), 21, 181-186; D. Heinrich, H. Berthold, "Application of Cold Sterilized Prothrombin Complex Concentrates in Man: Clinical and Serological Studies", The 13th International Congress of the World Federation of Hemophilia, Tel Aviv, July 8-13, 1979; W. Stephan, A. M. Prince, "Efficacy of Combined Treatment of Factor IX Complex (PPSB) with β-Propiolactone (b-PL) and Ultraviolet (UV) Irradiation", Haemostasis, (1981), 10, 67; A. M. Prince, W. Stephan, B. Brotman, "β-Propiolactone/Ultraviolet Irradiation: A Review of its Effectiveness for Inactivation of Viruses in Blood Derivatives", Rev. Infect. Dis., (1983), 5, 92-107; W. Stephan, A. M. Prince and R. Kotitschke, "Factor VIII Concentrate from Cold Sterilized Human Plasma", Develop Biol. Stand, (1983), 54, 491);

(4) heat applied to the product in the liquid state (S. S. Gellis, J. R. Neefe, J. Stokes Jr. et al, "Chemical, Clinical and Immunological Studies on the Products of Human Plasma Fractionation, XXXVI Inactivation of the Virus of Homologous Serum Hepatitis in Solutions of Normal Human Serum Albumin by Means of Heat", J. Clin. Invest., (1948), 27, 239-244; R. Murray, W. C. L. Diefenbach, "Effect of Heat on the Agent of Homologous Serum Hepatitis", Proc. Soc. Exp. Biol. Med., (1953), 84, 230-231; J. P. Soulier, C. Blatix, A. M. Courouce et al, "Prevention of Virus B Hepatitis (SH Hepatitis)", Am. J. Dis. Chid., (1972), 123, 429-434; T. Shikata, T. Karasawa, K. Abe et al, "Incomplete Inactivation of Hepatitis B Virus After Heat-Treatment at 60° C. for 10 hours", J. Infect. Dis., (1978), 138, 242-244; E. Tabor, R. J. Gerety, "The Chimpanzee Animal Model for non-A non-B Hepatitis: New Applications", W. Szmuness, H. J. Alter, J. E. Maynard eds. Viral Hepatitis: 1981 International Symposium., Philadelphia: The Franklin Institute Press, (1981), 305-317; Von. N. Heimburger, H. Schwinn, P. Gratz et al, "Faktor VIII-Konzentrate, Hochgereinigt und in Losung Erhitzt, Arzneim-Thromb/Drug Res., (1981), 31, 619; Tabor, G. Murano, P. Snoy et al, "Inactivation of Hepatitis B Virus by Heat in Antithrombin III Stabilized with Citrate", Thromb. Res., (1981), 22, 233-238; D. Menache, D. L. Aronson, "Measures to Inactivate Viral Contaminants of Pooled Plasma Products, R. Y. Dodd, L. F. Baker eds. Infection Immunity and Blood Transfusion Proc. XVII Annual Scientific Symposium, May 9-11, 1984. New York, Alan R. Loss, (1985), 407-423), or in the dry state (G. Dolana, D. Tse, W. Thomas et al, "Hepatitis Risk Reduction in Hemophilia: A Heated Factor VIII Preparation", J. Amer. Soc. Hematol., (1982), 60, (Suppl 1), 2102; F. R. Hollinger, G. Dolana, W. Thomas et al, "Reduction of Infectivity of Hepatitis B. Virus (HBV) and a non-A, non-B Hepatitis Agent by Heat Treatment of Human Antihemophilic Factor (AHF) Concentrates", L. R. Overby, F. Deinhardt, J. Deinhardt, eds., Viral Hepatitis: Second International Max von Pettenkofer Symposium, New York: Marcel Dekker, Inc., (1983) 245-246; F. B. Hollinger, G. Dolana, W. Thomas et al, "Reduction in Risk of Hepatitis Transmission by Heat-Treatment of a Human Factor VIII Concentrate", *J. Infect. Dis.*, (1984), 150, 250–262), (5) lipid solvents with the addition of surface active agents (A. M. Prince, B. Horowitz, B. Brotman et al, "Inactivation of Hepatitis B and Hutchinson Strain non-A, non-B Hepatitis Viruses by Exposure to Tween 80 and Ether", *Vox Sang*, (1984), 46, 36–43; A. M. Prince, B. Horowitz and B. Brotman, "Sterilisation of Hepatitis and HTLV-III Viruses By Exposure to Tri(n-Butyl)Phosphate and Sodium Cholate", *The Lancet*, 706–710, March 29, 1986), and lipid solvents without the additive of surface active agents (S. M. Feinstone, K. B. Mihalik, T. Kamimura et al, "Inactivation of Hepatitis B Virus and non-A, non-B Hepatitis by Chloroform, *Infect. Immunol.*, (1983), 41, 816–821; D. W. Bradley, J. E. Maynard, H. Popper et al, "Posttransfusion non-A, non-B Hepatitis: Physiochemical Properties of Two Distinct Agents", *J. Infect. Dis.*, (1983), 148, 254–265).

Neutralization by specific antibody is limited by antibody availability (hepatitis B virus only, so far), (Tabor et al, *Lancet*, (1980), supra and Brummelhuis et al, *Vox Sang*, (1983), supra) ultraviolet irradiation and thermal inactivation methods have been variably successful (S. S. Gellis, J. R. Neefe, J. Stokes, Jr., L. E. Strong, C. A. Janeway, G. Scatchard, "Chemical, Clinical and Immunological Studies on the Products of Human Plasma Fractionation. XXXVI. Inactivation of the Virus of Homologous Serum Hepatitis in Solutions of Normal Human Serum Albumin by Means of Heat", *J. Clin. Invest.*, (1947), 27, 239–244; N. Heimburger, H. Schwinn, R. Mauler, "Factor VIII Concentrate, Hepatitis-Safe: Progress in the Treatment of Hemophilia A", *Die gelben Hefte*, (1980), 20, 165–174; M. Colombo, V. Carnelli, C. Gazengel, P. M. Mannucci, G. F. Savidge, K. Schimpf, "Transmission of non-A, non-B Hepatitis by Heat-Treated Factor VIII Concentrate", *Lancet*, (1985), July 1–4; F. E. Preston, C. R. M. Hay, M. S. Dewar, M. Greaves, D. R. Triger, "Non-A, non-B Hepatitis and Heat Treated Factor VIII Concentrates", *Lancet*, (1985), July, 213; C. Rouzioux. S. Chamaret, L. Montagnier, V. Carnelli, G. Rolland, P. M. Mannucci, "Absence of Antibodies to AIDS Virus in Haemophiliacs Treated with Heat-Treated Factor VIII Concentrate, *Lancet*, (1985), February, 271–272; P. B. A. Kernoff, E. J. Miller, G. F. Savidge, S. J. Machin, M. S. Dewar, F. E. Preston, "Wet Heating for Safer Factor VIII Concentrate?" *Lancet*, 1985, September, 721), and beta-propiolactone chemically alters proteins and its carcinogenic properties constitute a hazard to personnel handling it.

U.S. Pat. Nos. 4,481,189 and 4,540,573, the entire contents of which are incorporated by reference herein, describe the use of organic solvent/detergent pairs to reduce by several orders of magnitude the infectivity of hepatitis viruses and certain other viruses contained in plasma and plasma products or added thereto.

Solvent/detergent treatment under appropriate conditions of temperature and contact time effectively disassembles viruses that have envelope proteins associated with lipid, while having negligible effect on the molecular conformations and biological activities of sensitive blood plasma proteins.

The independent effects of organic solvents and detergents in disassembling and attenuating viruses can be facilitated by the presence of both. Removal of detergents, as well as organic solvents, from biological products may be necessary, especially if a particular detergent is not well tolerated by humans or whatever biological system within which the product is to be used.

Other examples of virus inactivation reagents applied to blood include merocyanine, beta-propiolactone and cis-platin.

Other methods used to achieve removal of lipid/detergent mixed micelles from membrane protein complexes may be applicable to removal of the same from plasma products and other biologic products. These have been based on differences in size, buoyant density, charge, binding affinity, phase partitioning and solvent partitioning (A. Helenius and K. Sinous, "Solubilization of Membranes by Detergents", *Biochem. Biophys. ACTA*, (1975), 415, 29–79).

In the instance of whole blood plasma, blood serum, cryodepleted plasma or cryoprecipitate for direct use in transfusion, implementation of virus sterilization techniques has not been heretofore reduced to practice. Methods of heat sterilization result in unwanted protein denaturation. Immune neutralization is limited, at this time, to hepatitis B virus. Beta-propiolactone/UV treatment results in the destruction of sensitive coagulation factors, e.g., anti-hemophilic factor. Organic solvent/detergent mixtures require implementation of expensive and inconvenient fractionation steps to remove the reagents which cannot be applied conveniently to single units of plasma intended for transfusion or to plasma pools.

Another difficulty in preparing virus sterilized plasma is in filtering the plasma following treatment to maintain bacterial sterility without loss of fibrinogen, antihemophilic factor or other labile proteins.

Thus, because virus sterilization techniques have not been applied to whole blood plasma, serum, cryoprecipitate, cryopoor plasma, virus infectivity upon infusion remains, estimated at 0.05% for hepatitis B and 3% for non-A, non-B hepatitis transmission.

Exogenous chemicals are frequently added to biological mixtures to stimulate synthesis, inactivate viruses contained therein and to stabilize or purify desired components present in the mixture. It is generally desirable to remove these chemicals without otherwise affecting the structure and function of the desired components. For example, the synthesis of certain desired biological products can be induced or enhanced in cell cultures by introduction of phorbol esters into the culture fluid. For example, mezerein may be used to induce gamma interferon production by cultured leukocytes (Y. K. Yip, R. H. L. Pang, J. O. Oppenheim, M. S. Nashbar, D. Henriksen, T. Zerebeckyj-Eckhardt, J. Vilcek, "Stimulation of Human Gamma Interferon Production by Diterpene Esters", *Infect. and Immun.*, (1981) 131–139) or to augment secretion of tumor necrosis factor by cells that produce it (B. D. Williamson, E. A. Carswell, B. Y. Rubin, J. S. Prendergast, H. J. Old, "Human Tumor Necrosis Factor Produced by Human B-cells Lines: Synergistic Cytoxic Interaction with Human Interferon", *Proc. Natl. Acad. Sci., USA*, (1981), 80, 5397–5401).

Before use in man, phorbol esters must be removed from lymphokine preparations because of the carcinogenic properties of these compounds. Heretofore, phorbol esters have been removed by precipitation, chromatographic, or molecular exclusion processes, (B. Y. Rubin, S. L. Anderson, S. A. Sullivan, B. D. Williamson, E. A. Carswell, L. J. Old, "Purification and Characterization of a Human Tumor Necrosis Factor from the LukII Cell Line", *Proc. Natl. Acad. Sci., USA*, (1985), 82, 6637–6641).

Process chemicals are also used to purify biopolymers such as blood proteins. For example, polyethylene glycol 4000 (PEG) is used in the purification of antihemophilic factor and a step or steps must be taken to remove PEG.

Dimethylsulfoxide has been added to red blood cell concentrates to stabilize them, especially against freezing, and diethylhexylphthalate also has been shown to increase the stability of red blood cells to storage.

SUMMARY OF THE INVENTION

It is an object of the present invention to remove virus inactivating solvents and/or detergents and/or other process chemicals, such as phorbol esters, from biological materials, without destroying the properties of the desired components. This object and other objects are provided by the present invention wherein lipid soluble process chemicals, e.g., virus inactivating solvents and/or certain detergents and/or phorbol esters, are extracted from biological materials, e.g., labile biological materials, using an organic alcohol whose solubility in an aqueous solution at the temperature of use is $\leq 0.6\%$ and/or a halogenated hydrocarbon containing more than one type of halogen atom, e.g., F and Cl and preferably also containing an ether linkage.

Quite surprisingly, applicants have found two classes of organic solvents which combine excellent solvation of process chemicals with excellent compatibility with labile proteins and/or cells. It is especially surprising that these solvents can extract non-ionic detergents such as "TWEEN 80" and "TRITON X-45" from aqueous solutions. It is further surprising that they can be used to improve the physical properties, such as filterability, of the biological mixture without loss of valuable constituents.

The present invention concerns methods for removing virus attenuating solvents from biological materials to which such solvents have been added. The present invention also concerns removal of certain virus attenuating detergents from biological materials to which such detergents have been added together with or without solvents.

The present invention also concerns methods for removing other virucidal agents from biological materials.

The present invention further concerns methods for removing process chemicals added as stabilizers to biological materials.

The present invention also further concerns methods for removing process chemicals used in the purification of biological materials.

The present invention is also directed to a process to prepare virus-sterilized cell components, e.g., red blood cells or platelets, wherein a virus sterilizing agent, e.g., merocyanine or a psoralin, is extracted by the inventive method.

The present invention additionally concerns methods for removing naturally occurring lipids and other endogenous, e.g., pyrogens, or exogenous, e.g., "TWEEN 80", "TRITON X-45" and TNBP, lipid soluble compounds from biological materials, such removal resulting in improved properties of said materials, e.g., filterability, stability, or rendering virus sterilization reagents more effective.

The present invention also concerns methods for the removal of chemical inducers such as lymphokine inducing phorbol esters from biological materials.

The present invention further concerns methods for single or multiple extractions of solvents, certain detergents, phorbol esters or other process chemicals from biological materials by using an organic alcohol whose solubility in an aqueous solution is≦0.6% and/or a halogenated hydrocarbons containing more than one type of halogen atom.

The present method involves bringing a biological material containing the lipid soluble chemicals, e.g., virus attenuating reagent, e.g., a solvent, and/or detergents, into contact with an effective amount of an organic alcohol whose solubility in an aqueous solution at the temperature of use is≦0.6% and/or a halogenated hydrocarbon containing more than one type of halogen atom, e.g., fluorine and a chlorine. The resultant mixture is agitated; thereafter phase separation occurs by sedimentation or can be facilitated by centrifugation. When using organic alcohols according to the present invention, the upper phase contains the organic alcohol and the extracted process chemicals; the lower phase is relatively free of process chemicals and contains product. When using a halogenated hydrocarbon according to the present invention, the lower phase contains the halogenated hydrocarbon and process chemicals; the upper phase is relatively free of process chemicals and contains product.

The present invention also concerns a protein-containing blood product selected from the group consisting of blood plasma, serum, cryoprecipitate and cryodepleted plasma, the blood product having been previously virus infected and treated so as to have an extent of inactivation of virus greater than 6 logs for said virus, the blood product having a retention of functional activity for particular biological active blood proteins of at least 45% and having no more than physiologically acceptable levels of lipid soluble chemicals.

The present invention further concerns the removal of process agents added to blood cells, without disruption of the cells.

The present invention is also directed to a method for improving the filterability of a biological material, such as whole blood plasma, blood serum, cryodepleted plasma, cryoprecipitate, virus sterilized whole blood plasma, virus sterilized blood serum, virus sterilized cryodepleted plasma or virus sterilized cryoprecipitate, comprising contacting the biological material with an effective amount of an organic alcohol whose solubility in an aqueous solution at the temperature of use is≦0.6% and/or a halogenated hydrocarbon containing more than one type of halogen, agitating the resultant mixture and achieving a phase separation of the biological material and the organic alcohol and/or halogenated hydrocarbon.

BRIEF DESCRIPTION OF THE DRAWING

FIG. 1 is a plot depicting the retention of AHF activity and the removal of "TRITON X-45" by using organic alcohols according to the present invention.

DETAILED DESCRIPTION OF THE INVENTION

Blood is made up of solids (cells, i.e., erythrocytes, leucocytes, and thrombocytes) and liquid (plasma). The cells contain potentially valuable substances such as hemoglobin, and they can be induced to make other potentially valuable substances such as interferons, growth factors, and other biological response modifiers. The plasma is composed mainly of water, salts, lipids and proteins. The proteins are divided into groups called fibrinogen, serum globulins and serum albumin. Typical antibodies (immune globulins) found in human blood plasma include those directed against infectious hepatitis, influenza H, etc.

Blood transfusions are used to treat anemia resulting from disease or hemorrhage, shock resulting from loss of plasma proteins or loss of circulating volume, diseases where an adequate level of plasma protein is not maintained, for example, hemophilia, and to bestow passive immunization.

Whole blood must be carefully typed and cross matched prior to administration. Plasma, however, does not require prior immunological testing. For certain applications, only a proper fraction of the plasma is required, such as factor VIII for treatment of hemophilia or von Willebrand's disease.

With certain diseases one or several of the components of blood may be lacking. Thus the administration of the proper fraction will suffice, and the other components will not be "wasted" on the patient; the other fractions can be used for another patient. The separation of blood into components and their subsequent fractionation allows the cells and the proteins to be concentrated, thus permitting concentrates to be treated. Of great importance, too, is the fact that the plasma fractions can be stored for much longer periods than whole blood and they can be distributed in the liquid, the frozen, or the dried state. Finally, it allows salvaging from blood banks the plasma portions of outdated whole blood that are unsafe for administration as whole blood.

Cells found in blood include red cells, various types of leukocytes or white cells, and platelets. Fractionation of cell types typically utilizes centrifugation, but may involve other forms of differential sedimentation through addition of rouleaux enhancing agents such as hydroxyethyl starch, separations based on immunological specificity, etc.

· Proteins found in human plasma include prealbumin, retinol-binding protein, albumin, alpha-globulins, beta-globulins, gamma-globulins (immune serum globulins), the coagulation proteins (antithrombin III, prothrombin, plasminogen, antihemophilic factor (factor VIII), fibrin-stabilizing factor-factor XIII, fibrinogen), immunoglobins (immunoglobulins G, A, M, D, and E), and the complement components. There are currently more than 100 plasma proteins that have been described. A comprehensive listing can be found in "The Plasma Proteins", ed. Putnam, F. W., Academic Press, New York (1975).

Proteins found in the blood cell fraction include hemoglobin, fibronectin, fibrinogen, enzymes of carbohydrate and protein metabolism, platelet derived growth factor etc. In addition, the synthesis of other proteins can be induced, such as interferons and growth factors.

A comprehensive list of inducible leukocyte proteins can be found in Stanley Cohen, Edgar Pick, J. J. Oppenheim, "Biology of the Lymphokines", Acamedic Press, N.Y. (1979).

Blood plasma fractionation generally involves the use of organic solvents such as ethanol, ether and polyethylene glycol at low temperatures and at controlled pH values to effect precipitation of a particular fraction containing one or more plasma proteins. The resultant supernatant can itself then be precipitated and so on until the desired degree of fractionation is attained. More recently, separations are based on chormotographic processes. An excellent survey of blood fractionation appears in *Kirk-Othmer's Encylopedia of Chemical Technology*, Third Edition, Interscience Publishers, Volume 4, pages 25 to 62.

The major components of a cold ethanol fractionation are as follows:

| Fraction | Proteins |
| --- | --- |
| I | fibrinogen; cold insoluble globulin; factor VIII; properdin |
| II and III | IgG; IgM IgA; fibrinogen;beta-lipoprotein; prothrombin; plasminogen; plasmin inhibitor; factor V; factor VII; factor IX; factor X: thrombin; antithrombin; isoagglutinins; ceruloplasmin; complement C'1, C'3 |
| IV-1 | $alpha_1$-lipoprotein, ceruloplasmin; plasmin-inhibitor; factor IX; peptidase; alpha-and-beta-globulins |
| IV-4 | transferrin; thyroxine binding globulin; serum esterase; $alpha_1$-lipoprotein; albumin; alkaline phosphatase |
| V | albumin; alpha-globulin |
| VI | $alpha_1$-acid glycoprotein; albumin |

The above fractionation scheme can serve as a basis for further fractionations. Fraction II and III, for example, can be further fractionated to obtain immune serum globulin (ISG).

Another fractionation scheme involves use of frozen plasma which is thawed into a cryoprecipitate containing AHF (antihemophilic factor) and fibronectin and a cryosupernatant. The cryoprecipitate is then fractionated into fibronectin and AHF.

Polyethylene glycol has been used to prepare high purity AHF and non-aggregated ISG.

High risk products with respect to the transmission of hepatitis B and non-A, non-B are fibrinogen, AHF and prothrombin complex, and all other blood protein preparations except immune serum globulin prepared for intramuscular injection and, because they are pasteurized, albumin solutions.

The methods of the present invention are applicable to biological materials including blood, blood cells, blood plasma, blood fractions thereof, and blood proteins such as those discussed hereinabove, cryoprecipitate, cryodepleted serum and more generally to biological cells and fluids, e.g., normal cells, cancer cells, exudate from cancer cells grown in culture, exudate from normal cells grown in culture, cells from hybridomas, products of gene splicing, plant cell concentrates, plant cell suspensions, extracts of animal tissue, extracts of plant tissue and microorganisms.

Non-limiting examples of organic alcohols for use in the present invention include hexanol, heptanol, 1-octanol, 2-octanol, 1-nonanol, 1-decanol and undecanol.

Non-limiting examples of halogenated (e.g., containing fluorine, chlorine, iodine and/or bromine) hydrocarbons for use in the present invention include 1,2,2-trifluorotrichloroethane, "ETHRANE" (enflurane; 2-chloro-1,1,2-trifluoroethyl difluoromethyl ether), "FORANE" (isofluorane; 1-chloro-2,2,2-trifluoroethyl difluoromethyl ether). Preferred halogenated hydrocarbons according to the present invention contain fluorine, chlorine and ether.

The preferred solvents for use in the present invention are liquid at the temperature of use, immiscible with the aqueous solutions being extracted, non-denaturing to proteins and to cells under the conditions of use, easily removed, non-explosive, and non-toxic in the quantities remaining in the biological solution under the conditions of use.

After use, the organic alcohol and/or halogenated hydrocarbon can be removed by extraction with edible oils, e.g., vegetable oils, by lyophilization, or by other standard techniques, such as diafiltration or gel exclusion chromatography.

Extraction of complex mixtures with the alcohols or halogenated hydrocarbons according to the present invention would reduce the lipid content of the mixture. This may improve the stability of the mixture, and, if used prior to virus inactivation, may directly or indirectly contribute to virus safety.

Di-or trialkylphosphates, detergents and surfactants for removal by the process of the present invention are described in U.S. Pat. Nos. 4,540,573 and 4,481,189.

Exemplary ranges for solvent, detergent and organic alcohol or halogenated hydrocarbon are as follows:

| Solvent | 1000–20,000 ppm |
| --- | --- |
| Detergent | 1000–10,000 ppm |
| Organic alcohol or halogenated hydrocarbon | 5–50% of biological fluid (weight %) |

The preferred ranges for each of the above is lowest possible value commensurate with effective virus inactivation and quantitative extraction of solvent and detergent.

Normal and preferred extraction conditions are as follows:

| normal temperature | 0° C. to 35° C., |
| --- | --- |
| preferred | ambient, |
| normal exposure time | 10–60 minutes; |
| preferred | 30 minutes. |

The organic alcohol and/or halogenated hydrocarbon as described above can be used for extraction purposes in a continuous flow extractor, such as a Karr Reciprocating Plate Extraction Column (Chem-Pro Corporation).

The present invention is particularly directed, inter alia, to producing a blood cell and protein-containing composition such as blood, red blood cells, platelets, leukocytes, blood plasma, blood plasma fractions, etc., which is substantially free of infectious virus, yet which retains a substantial amount of cellular structure and function and enzymatically or biologically active (undenatured) protein and from which process chemicals have been removed so that the resultant composition has no more than physiologically acceptable levels of such process chemicals.

Biological fluids for use according to the present invention include mammalian blood, blood plasma, blood plasma fractions, precipitates from blood fractionation and supernatants from blood fractionation, platelet concentrates, white cell (leukocyte) concentrates, and leukocyte-poor packed red cells, as well as platelet rich plasma, platelet concentrates and platelet poor plasma, including packed cell masses comprising the white buffy coat consisting of white blood cells above packed red cells. Also contemplated is the treatment of masses containing concentrates of granulocytes, monocytes, cells capable of producing interferon, tumor necrosis factor (TNF), lymphotoxin (LT) and other immune modulators and lymphokines, e.g., interlukin-2 (IL-2), interlukin-3 or CSF, or media separated from such concentrates or suspensions.

Inactivation of virus is obtained by use of the present invention to the extent of at least "6 logs", i.e., virus in a serum is totally inactivated to the extent determined by infectivity studies where that virus is present in the untreated serum in such a concentration that even after dilution to $10^6$, viral activity can be measured. Examples of infectious virus are as follows: AIDS virus (HTLV III/LAV) and hepatitis B, and non-B non-A (NANB) hepatitis virus. Other viruses inactivated during the course of the present invention include, for example, cytomegaloviruses, Epstein Barr viruses, lactic dehydrogenase viruses, herpes groups viruses, rhabdoviruses, leukoviruses, myxoviruses, alphaviruses, arboviruses (group B), paramyxoviruses, arenaviruses, coronaviruses, retroviruses including HTLV I and HTLV II, and animal leukemia viruses.

According to the present invention, there is contemplated a protein-containing composition, particularly whose blood plasma or whole blood serum having an extent of inactivation of virus greater than 6 logs of virus, such as AIDS virus, hepatitis B virus and non-A non-B hepatitis virus, having a retention of functional activity for particularly biologically active proteins of at least 45%, preferably at least 75%, more preferably at least 85%, even more preferably at least 95% and more preferably 98% to 100%, and having no more than physiologically acceptable levels of lipid soluble process chemicals.

The (virus sterilized) whole blood plasma, blood serum, cryoprecipitate or cryodepleted plasma according to the present invention can be transfused directly into a patient, e.g., mammal, e.g., human. Alternatively, the (virus sterilized) whole blood plasma, blood serum, cryodepleted plasma or cryoprecipitate according to the present invention can be fractionated to prepare purified plasma protein derivatives (such derivatives can be transfused directly into a patient, e.g., a human patient).

The whole blood plasma or blood serum according to the present invention can also be used in cell cultures and as a quality control reagent.

Furthermore, non-blood sources including, for example, normal (noncancerous) or cancer cells, exudate from cancer or normal cells grown in culture, hybridomas and products from gene splicing, plant cell concentrates or suspensions, extracts of animal or plant tissues, or microorganisms can be used as the biological fluid in the present invention.

The present invention will now be described with reference to the following non-limiting examples.

EXAMPLES

Example 1:

Extraction of Process Chemicals from Saline

Results of the efficiency of extraction of TNBP and selected non-ionic detergents from saline by two alcohols, namely, 1-pentanol and 2-octanol, by "FORANE" and by soybean oil, provided for comparative purposes only. All of the extraction media were found to remove TNBP efficiently. By contrast, little "TWEEN" extraction was achieved with soybean oil or the longer chain alcohol, while 28–42% removal was achieved with 5% 1-pentanol and 87% extraction was achieved with 20% "FORANE". Efficient extraction of "TRITON" X45 was provided by both of the alcohols evaluated and by "FORANE"; soybean oil was less effective. As the hydrophilicity of the "TRITON" increases, the extraction efficiency declined for 1-pentanol, 2-octanol and soybean oil. Results with nonoxynol also demonstrated the improved extraction efficiency with the alcohols as compared to soybean oil.

TABLE 1

Extraction of Process Chemicals from Saline

|  | Percent Extraction with | | | | 20% soybean oil (comparison) |
|---|---|---|---|---|---|
|  | 5% 1-pentanol | 5% 2-octanol | "FORANE" 5% | 20% |  |
| 1% TNBP | 99 | 99 | 99 | 99 | 97 |
| 1% "TWEEN 80" | 28–42 | 0–12 | 85 | 87 | 0–4 |
| 1% "TRITON X45" | 97 | 83–96 | 99 | 99 | 37 |
| 1% "TRITON X114" | 91 | 94 | 99 | 99 | 25 |
| 1% "TRITON X100" | 92 | 60 | 99 | 99 | <1 |
| 1% Nonoxynol | 92 | 49 | ND | | 11 |

ND - No data

Example 2:

Extraction of Process Chemicals From Plasma

Table II provides data on the extraction of TNBP and each of several detergents from plasma. The results are in general agreement with those observed extracting from saline.

TABLE II

Extraction of Process Chemicals from Plasma

|  | Percent Extraction with | | | |
|---|---|---|---|---|
| Process Chemical | 5% 1-pentanol | 5% 2-octanol | "FORANE" 5% | 20% |
| 2% TNBP | 98 | 98 | 94 | 96 |
| 1% "TWEEN 80" | 7 | 21 | ND | 66 |
| 1% "TRITON X45" | 80 | 62 | 91 | 99 |
| 1% "TRITON X114" | 75 | 33 | 96 | 96 |
| 1% "TRITON X100" | 65 | 19 | 95 | 96 |

ND - No data

Example 3:

Recovery of AHF Procoagulant Activity Following Extraction

Data on the recovery of AHF on extraction of an AHF concentrate or of plasma is provided in Table III. AHF recovery with 1-pentanol was approximately 1%. AHF recovery on extraction with 2-octanol and with "FORANE" was approximately 90% and 100%, respectively.

TABLE III

Recovery of AHF Procoagulant Activity Following Extraction

| Extractant | Protein Solution | AHF Activity (units/mL) | | % Recovery |
|---|---|---|---|---|
|  |  | Before | After |  |
| 5% 1-pentanol | 1 | 2.25 | 0.02 | 1 |
|  | 2 | 1.26 | 0.01 | 1 |
| 5% 2-octanol | 1 | 2.65 | 2.35 | 89 |

TABLE III-continued

Recovery of AHF Procoagulant Activity Following Extraction

| Extractant | Protein Solution | AHF Activity (units/mL) | | % Recovery |
|---|---|---|---|---|
|  |  | Before | After |  |
|  | 2 | 1.26 | 1.15 | 91 |
| 5% "FORANE" | 1 | 2.65 | 2.69 | 102 |
|  | 2 | ND | | |

1 - AHF Concentrate
2 - Plasma
ND - No data

Example 4:

Inactivation of Virus in Whole Plasma with TNBP/Detergent Mixtures and Reagent Removal by Extraction with "FORANE"

Plasma harvested from donated blood in the presence of anticoagulants was treated by the addition of solvent or solvent/detergent pairs to inactivate virus. Four liters of plasma were placed in each of four vessels. Virus attenuating organic solvent with or without detergent was added and dispersed by stirring. In these examples, one vessel received 2% TNBP and was incubated at 37° C., the second received 1% TNBP (tri-n-butylphosphate) and 1% "TWEEN 80" and was incubated at 30° C., the third received 1% TNBP and 1% "TRITON X 45" and was incubated at 30° C. and the fourth was the control.

After 4 hours, each was extracted with 20% "FORANE" for 30 minutes and the upper aqueous layer was analyzed for labile clotting factors and the level of residual TNBP and detergent. Separate parallel experiments evaluated virus kill following the addition of test virus suspensions. The results are summarized in Table IV and V below.

TABLE IV

| | Virus Kill ($\log_{10}$ decline) | | |
|---|---|---|---|
| Virus | 2% TNBP | 1% TNBP/ 1 "TWEEN 80" | 1% TNBP/ "TRITON X 45" |
| VSV | 4.2 | 5.2 | 5.2 |
| Sindbis Virus | 5.2 | 5.5 | 5.5 |
| HIV | 3.6 | 3.1* | — |
| NANBHV | 5.0 | — | — |
| HBV | 6.0 | — | — |

*means after 15 minutes
— means not done

TABLE V

Coagulation Factor Activity and Level of Residual Reagents

| | Percent Recovery* | | |
|---|---|---|---|
| Factor | 2% TNBP | 1% TNBP/ 1% "TWEEN 80" | 1% TNBP/1% "TRITON X 45" |
| Factor II | 105 | 99 | 108 |
| Factor VII | 95 | 93 | 101 |
| Factor VIII | 81 | 107 | 92 |
| Factor IX | 89 | 101 | 89 |
| Factor X | 98 | 101 | 97 |
| anti-thrombin III | 100 | — | — |
| TNBP/ Detergent (μg/ml) | 9/na | 1/<100 | 1/<100 |

*means as compared to untreated
— means not done
na means not applicable

Example 5:

Removal of TNBP and "TRITON X-45", Used for the Inactivation of Virus, From a Solution Containing Antihemophilic Factor (AHF), With Alcohols An AHF concentrate prepared form human plasma was treated with 0.3% TNBP and 1% "TRITON X-45" to inactivate virus. Following treatment, the solution was extracted one time with 10% (w/v) of alcohol by mixing for a period of 30 minutes at ambient temperature. The quantity of residual AHF and "TRITON X-45"0 present in the aqueous solution was measured and compared with the unextracted control. The results presented in the Table VI and FIG. 1 indicate that only those alcohols with an aqueous solubility of less than (or equal to) 0.6% (w/v) provided excellent removal of "TRITON X-45" and excellent (>60%) retention of AHF clotting activity.

TABLE VI

| Alcohol | Aqueous Solubiltiy (g %) | AHF (% Retention) | "TRITON X-45" (% Removal) |
|---|---|---|---|
| tert.-amyl alcohol | 12.5 | 1 | 98 |
| amyl alcohol | 2.3 | 1 | 100 |
| isoamyl alcohol | 2.0 | 1 | 100 |
| hexanol | 0.6 | 63 | 100 |
| heptanol | 0.2 | 98 | 100 |
| 1-octanol | 0.05 | 96 | 100 |
| 2-octanol | 0.05 | 93 | 100 |
| 1-nonanol | <0.05 | 100 | 100 |
| 1-decanol | <0.05 | 100 | 100 |
| undecanol | <0.05 | 94 | 100 |

Example 6:

Removal of TNBP and Either "TRITON X-45" or "TWEEN 80" From a Solution Containing Antihemophilic Factor (AHF), With Halogenated Hydrocarbons An AHF concentrate prepared from human plasma was treated with 0.3% TNBP and either 1% "TRITON X-45" or 1% "TWEEN 80" to inactivate virus. Following treatment, the solution was extracted one time with 5% (w/v) of a halogenated hydrocarbon by mixing for a period of 30 minutes at ambient temperature. The quantity of residual AHF, TNBP and detergent present in the aqueous solution was measured and compared with the unextracted control. The results are summarized in Table VII.

TABLE VII

| Halogenated Hydrocarbon | % Retention AHF | Percent Removal TNBP | "TRITON X-45" | "TWEEN 80" |
|---|---|---|---|---|
| 1,2,2-Trifluoro-trichloroethane | 98 | 93 | 8 | 3 |
| "FORANE" | 100 | 99 | 99 | 87 |
| Ethrane | 100 | 99 | 99 | na[a] |
| Perfluorodecalin | 107 | 14 | 0 | 0 |
| Perfluorohexane | 98 | 27 | 0 | 0 |
| Perfluorotributyl amine | 112 | 31 | 0 | 3 |
| Perfluorocyclic ether | na | na | 0 | na |

[a]na = not available

Example 7:

Sterilization of a Red Cell Concentrate With Merocyanine 540 and Its Extraction With "FORANE"

Whole human blood was centrifuged and the lower layer containing the red blood cells (RBC) was washed twice with phosphate buffered saline. The washed cells were diluted in buffered saline to a final concentration of $3 \times 10^8$ cells/mL. Vesicular stomatitis virus was added followed by merocyanine 540 at a final concentration of 40 µg/mL. The mixture was exposed to a white fluorescent light source at an approximate intensity of $2.5 \times 10^{-2}$ J/sec for a period of 60 minutes. At the conclusion of the reaction, the quantity of residual virus was measured. Separately run samples were extracted with 10% "FORANE" and the degree of red cell retention and merocyanine removal were measured. The results are summarized in Table VIII.

TABLE VIII

Treatment of Red Blood Cells with Merocyanine and Extraction with "FORANE"

A. Virus Kill

| | Tissue Culture Infectious Doses $TCID_{50}$ ($\log_{10}$) |
|---|---|
| Initial Virus Titer | 3.7 |
| Final Virus Titer | <−0.5 |
| Control (no light) | 3.7 |
| Total Virus Kill | >4.2 |

B. Red Blood Cell Retention on Extraction with "FORANE"

| | RBC/mL ($\times 10^{-8}$) |
|---|---|
| Before | 3.0 |
| After | 2.9 |
| Retention | 97% |

C. Merocyanine Removal from Saline on Extraction with "FORANE"

| | $A_{540}$ |
|---|---|
| Before | 1.222 |
| After | 0.215 |
| % Removal | 83% |

Example 8:

Preparation of Virus Sterilized Cryoprecipitate

Ten units of single donor cryoprecipitate were solubilized in 0.02M Tris-HCl, pH 7.2, containing 0.1M sodium chloride. The units were pooled and vesicular stomatitis virus (VSV), sindbis virus, or Sendai virus were added to monitor virucidal action. Aliquots were treated with 1% TNBP and 1% "TRITON X-45" at 30° C. for 6 hours to inactivate virus. Following the reaction, the pool was split and extracted two times, either with 10% "FORANE" or with a mixture of 10% "FORANE" and 5% heptanol. The extracted cryoprecipitate was sterile filtered and lyophilized to remove the solvents. The extent of virus kill and the levels of residual TNBP, "TRITON X-45" and AHF were measured. The results are indicated in Table IX.

TABLE IX

A. Virus Kill

| | $TCID_{50}$ ($\log_{10}$) | | |
|---|---|---|---|
| | VSV | Sindbis | Sendai |
| Initial Virus Titer | 4.0 | 5.0 | 5.5 |
| Final Virus Titer | <−0.5 | <−0.5 | <−0.5 |
| Total Virus Kill | >4.5 | >5.5 | >6.0 |

B. AHF Recovery and Reagent Removal

AHF

TABLE IX-continued

| Solvent | Recovery % | Percent Removal TNBP | "TRITON X-45" |
|---|---|---|---|
| "FORANE" | 95 | 99.88 | 96 |
| "FORANE"/Heptanol | 80 | 99.99 | >97 |

Example 9:

Effect of Extraction of Plasma with "FORANE" or 2-Octanol on Plasma Filterability Plasma was extracted with either 10% "FORANE" or 10% 2-octanol for 30 minutes at ambient temperature. At the end of the extraction, attempts were made to pass the plasma through Pall 47 mm NR filters of varying porosity under 5 to 10 psi nitrogen pressure in order to determine the minimum porosity which would still permit a flow rate of 12 mL/minute. The results given below in Table X indicate that extraction of plasma with either "FORANE" or 2-octanol improves the filterability of plasma, without significant loss of labile protein activity.

TABLE X

| A. Filterability | |
|---|---|
| Solvent Extractant | Minimum Porosity of Filter which Provides a Flow Rate of 12 mL/minute |
| None | 3 micron |
| "FORANE" | <0.45 micron |
| 2-Octanol | <1.2 micron |

| B. Protein Functional Activity | | |
|---|---|---|
| | % Retention | |
| Protein | "FORANE" | 2-Octanol |
| AHF | 98 | 95 |
| Factor IX | 99 | 99 |
| Antithrombin III | 100 | 100 |

Example 10:

Depyrogenation of AHF Concentrate with 2-octanol or "FORANE"

AHF concentrate containing 6.4 ng/ml of endotoxin was extracted by mechanically shaking with 10% (v/v) 2-octanol or "FORANE" for 30 minutes at 24° C. After separation of the extractant by centrifugation, the pyrogen level was determined by the Limulus Amebocyte Lysate assay with a sensitivity of 0.025 ng/ml of endotoxin. The effect of these treatments is shown below in Table XI. Controls in which pyrogen-free material was extracted and also to which low levels of endotoxin were added after extraction were included to show that extraction per se did not affect the reliability of the assay. More than 90% of the original AHF activity was retained following the extraction.

TABLE XI

| Extractant | none | 2-octanol | "FORANE" |
|---|---|---|---|
| endotoxin (ng/ml) | 6.4 | <0.025 | 1.6 |
| % removed | [0] | >99.6 | 75 |

It will be appreciated that the present specification and claims are set forth by way of illustration and not limitation and that various modifications and changes may be made without departing from the spirit and scope of the present invention.

What is claimed is:

1. A method of removing exogenous or endogenous lipid soluble chemicals from a biological material containing said lipid soluble chemicals, the method comprising bringing said biological material containing said lipid soluble chemicals into contact with an effective amount of a halogenated hydrocarbon containing more than one type of halogen and on ether linkage, agitating the resultant mixture and achieving a phase separation of the biological material and the halogenated hydrocarbon.

2. A method according to claim 1, wherein the biological material contains an endogenous lipid soluble chemical and the endogenous lipid soluble chemical is a pyrogen.

3. A method according to claim 1, wherein the halogenated hydrocarbon is separated from the biological material by sedimentation or centrifugation.

4. A method according to claim 1 wherein the halogenated hydrocarbon comprises fluorine and chlorine.

5. A method according to claim 1, wherein the halogenated hydrocarbon is selected from the group consisting of isofluorane and 2-chloro-1,1,2-trifluoroethyl difluoromethyl ether.

6. A method according to claim 1, wherein the biological material is selected from the group consisting of whole blood plasma, blood serum, cryodepleted plasma or cryoprecipitate.

7. A method according to claim 1, wherein the biological material is a cell.

8. A method according to claim 7, wherein the biological material contains an exogenous lipid soluble chemical, wherein the cell is a red blood cell and wherein the exogenous chemical is merocyanine.

9. A method according to claim 1, wherein the biological material is selected from the group consisting of blood plasma, blood serum, cryoprecipitate, cryodepleted serum, Fraction I, Fraction II, Fraction III, Fraction IV-1, Fraction IV-4, Fraction V, Fraction VI, fibronectin, antihemophilic factor, prealbumin, retinol-binding protein, albumin, alpha-globulins, beta-globulins, gamma globulins, antithrombin III, prothrombin, plasminogen, fibrinogen, factor XIII, immunoglubin G, immunoglubin A, immunoglubin M, immunoglubin D and immunoglubin E, plasmin inhibitor, prothrombin, thrombin, antithrombin, factor V, factor VII, factor VIII, factor IX, factor X, normal cells, cancer cells, exudate from cancer cells grown in culture, exudate from normal cells grown in culture, cells from hybridomas, products of gene splicing, plant cell concentrates, plant cell suspensions, extracts of animal tissue, extracts of plant tissue and microorganisms.

10. A method for improving the filterability of a biological material comprising contacting said biological material with an effective amount of a halogenated hydrocarbon containing more than one type of halogen and an ether linkage, agitating the resultant mixture and achieving a phase separation of the biological material and the halogenated hydrocarbon.

11. A method according to claim 10, wherein the biological material is selected from the group consisting of whole blood plasma, blood serum, cryodepleted plasma, cryoprecipitate, virus sterilized whole blood plasma, virus sterilized blood serum, virus sterilized cryodepleted plasma and virus sterilized cryoprecipitate.

* * * * *